(12) United States Patent
Ruff

(10) Patent No.: US 8,679,551 B2
(45) Date of Patent: Mar. 25, 2014

(54) METHODS FOR TREATING GLUCOSE METABOLIC DISORDERS

(75) Inventor: Kevin J. Ruff, Carthage, MO (US)

(73) Assignee: ESM Holdings, LLC, Carthage, MO (US)

( * ) Notice: Subject to any disclaimer, the term of this patent is extended or adjusted under 35 U.S.C. 154(b) by 0 days.

(21) Appl. No.: 13/640,607

(22) PCT Filed: Apr. 12, 2011

(86) PCT No.: PCT/US2011/032103
§ 371 (c)(1),
(2), (4) Date: Dec. 19, 2012

(87) PCT Pub. No.: WO2011/130261
PCT Pub. Date: Oct. 20, 2011

(65) Prior Publication Data
US 2013/0089619 A1    Apr. 11, 2013

Related U.S. Application Data

(60) Provisional application No. 61/323,303, filed on Apr. 12, 2010.

(51) Int. Cl.
*A01N 65/00* (2009.01)

(52) U.S. Cl.
USPC .......................................................... 424/725

(58) Field of Classification Search
None
See application file for complete search history.

(56) References Cited

U.S. PATENT DOCUMENTS

2008/0063677 A1 *   3/2008   Long et al. ................... 424/401

* cited by examiner

*Primary Examiner* — Michael Meller
(74) *Attorney, Agent, or Firm* — Hoffmann & Baron LLP

(57) ABSTRACT

In one aspect, the invention relates to methods for treating a disease or condition associated with abnormal glucose metabolism. In another aspect, the invention relates to a method for reducing incidence or progression of insulin-dependent diabetes mellitus. The methods include orally administering to a mammal in need thereof an effective amount of a composition, which includes a naturally occurring material derived from eggshell, eggshell membrane, or a combination thereof.

1 Claim, No Drawings

METHODS FOR TREATING GLUCOSE METABOLIC DISORDERS

CROSS REFERENCE RELATED APPLICATION

The present invention asserts priority to U.S. Provisional Application Ser. No. 61/323,303, filed on Mar. 12, 2010, the contents of which are incorporated herein by reference.

INCORPORATION BY REFERENCE

The present invention incorporates by reference the disclosure of U.S. patent application Ser. No. 11/943,169, filed on Nov. 20, 2007, in its entirety.

BACKGROUND

Diabetes is one of the most prevalent chronic diseases in the United States, and it is a leading cause of death. Persons with diabetes are at risk for major complications, including diabetic ketoacidosis, end-stage renal disease, diabetic retinopathy and amputation. There are also a host of less directly related conditions, such as hypertension, heart disease, peripheral vascular disease and infections, for which persons with diabetes are at substantially increased risk. Accordingly, new methods of treating diabetes and diseases or conditions associated with abnormal glucose metabolism are needed.

SUMMARY OF THE INVENTION

These objectives, among others, are addressed by the present invention.

In one aspect, the invention relates to a method for treating a disease or condition associated with abnormal glucose metabolism in a mammal in need thereof. The method includes orally administering to the mammal an effective amount of a composition, which comprises a naturally occurring material derived from eggshell membrane.

In one embodiment, the disease or condition is insulin resistance.

In one embodiment, the disease or condition is glucose intolerance.

In one embodiment, the disease or condition is glucose non-responsiveness.

In one embodiment, the disease or condition is diabetes mellitus.

In one embodiment, the effective amount is effective to achieve at least a 0.2 percentage point decrease in hemoglobin A1c.

In one embodiment, the effective amount is effective to achieve at least a 1 percentage point decrease in hemoglobin A1c.

In one embodiment, the effective amount is effective to achieve at least a 2 percentage point decrease in hemoglobin A1c.

In one embodiment, the effective amount is effective to achieve at least a 3 percentage point decrease in hemoglobin A1c.

In one embodiment, the effective amount is effective to decrease a fasting blood glucose concentration in said mammal by at least 5 mg/dL.

In one embodiment, the effective amount is effective to decrease a fasting blood glucose concentration in said mammal by at least 10 mg/dL.

In one embodiment, the effective amount is effective to decrease a fasting blood glucose concentration in said mammal by at least 20 mg/dL.

In one embodiment, the naturally occurring material is selected from the group consisting of a hexosamine, glycosaminoglycan, hyaluronic acid, sialic acid, collagen, elastin, other egg proteins or glycoproteins, lysozyme, ovotransferrin, lysyl oxidase, and/or a combination thereof.

In one embodiment, the hexosamine is glucosamine and/or N-acetylglucosamine.

In one embodiment, the glycosaminoglycan is chondroitin sulfate, dermatan sulfate, keratin sulfate, heparin sulfate, and/or a combination thereof.

In one embodiment, the naturally occurring material is water soluble.

In one embodiment, the naturally occurring material is water insoluble.

In one embodiment, the naturally occurring material comprises the following in weight percent:
  a. about 0.25 to about 5 wt % hexosamine;
  b. about 0.3 to about 3 wt % glycosaminoglycan;
  c. about 0.5 to about 5 wt % hyaluronic acid;
  d. about 0.01 to about 2 wt % sialic acid; and/or
  e. about 5 to about 20 wt % collagen.

In one embodiment, the naturally occurring material is an eggshell membrane powder.

In one embodiment, the naturally occurring material is an eggshell membrane extract.

In one embodiment, the naturally occurring material is an eggshell membrane hydrosylate.

In one embodiment, the naturally occurring material is an eggshell membrane isolate.

In one embodiment, the mammal is insulin-dependent.

In one embodiment, the mammal has a fasting blood glucose concentration at least 100 mg/dL and at most 125 mg/dL.

In one embodiment, the mammal is diabetic.

In another aspect, the invention relates to a method for reducing incidence or progression of insulin-dependent diabetes mellitus in a mammal in need thereof. The method includes orally administering to the mammal an effective amount of a composition, which comprises a naturally occurring material derived from eggshell membrane.

In one embodiment, the disease or condition is insulin resistance.

In one embodiment, the disease or condition is glucose intolerance

In one embodiment, the disease or condition is glucose non-responsiveness.

In one embodiment, the disease or condition is diabetes mellitus.

In one embodiment, the effective amount is effective to achieve at least a 0.5 percentage point decrease in hemoglobin A1c.

In one embodiment, the effective amount is effective to achieve at least a 1 percentage point decrease in hemoglobin A1c.

In one embodiment, the effective amount is effective to achieve at least a 2 percentage point decrease in hemoglobin A1c.

In one embodiment, the effective amount is effective to achieve at least a 3 percentage point decrease in hemoglobin A1c.

In one embodiment, the effective amount is effective to decrease a fasting blood glucose concentration in said mammal by at least 5 mg/dL.

In one embodiment, the effective amount is effective to decrease a fasting blood glucose concentration in said mammal by at least 10 mg/dL.

In one embodiment, the effective amount is effective to decrease a fasting blood glucose concentration in said mammal by at least 20 mg/dL.

In one embodiment, the naturally occurring material is a therapeutically active material selected from the group consisting of eggshell membrane powder, an eggshell membrane hydrolysate, an eggshell membrane isolate, and combinations thereof.

In one embodiment, the naturally occurring material is selected from the group consisting of a hexosamine, glycosaminoglycan, hyaluronic acid, sialic acid, collagen, elastin, other egg proteins or glycoproteins, lysozyme, ovotransferrin, lysyl oxidase, and/or a combination thereof.

In one embodiment, the hexosamine is glucosamine and/or N-acetylglucosamine.

In one embodiment, the glycosaminoglycan is chondroitin sulfate, dermatan sulfate, keratin sulfate, heparin sulfate, and/or a combination thereof.

In one embodiment, the naturally occurring material is water soluble.

In one embodiment, the naturally occurring material is water insoluble.

In one embodiment, the naturally occurring material is eggshell membrane powder.

In one embodiment, the naturally occurring material is an eggshell membrane extract.

In one embodiment, the naturally occurring material is an eggshell membrane hydrolysate.

In one embodiment, the naturally occurring material is an eggshell membrane isolate.

In one embodiment, the mammal is insulin-dependent.

In one embodiment, the mammal has a fasting blood glucose concentration at least 100 mg/dL and at most 125 mg/dL.

In one embodiment, the mammal is diabetic.

In one embodiment, the naturally occurring material comprises the following in weight percent:
  a. about 0.25 to about 5 wt % hexosamine;
  b. about 0.3 to about 3 wt % glycosaminoglycan;
  c. about 0.5 to about 5 wt % hyaluronic acid;
  d. about 0.01 to about 2 wt % sialic acid; and/or
  e. about 5 to about 20 wt % collagen.

In a further aspect, the invention relates to a method for treating a disease or condition associated with abnormal glucose metabolism in a mammal in need thereof. The method includes orally administering to the mammal an effective amount of a composition, which comprises a naturally occurring material derived from fowl eggshells.

In one embodiment, the disease or condition is insulin resistance.

In one embodiment, the disease or condition is glucose intolerance

In one embodiment, the disease or condition is glucose non-responsiveness.

In one embodiment, the disease or condition is diabetes mellitus.

In one embodiment, the effective amount is effective to achieve at least a 0.2 percentage point decrease in hemoglobin A1c.

In one embodiment, the effective amount is effective to achieve at least a 1 percentage point decrease in hemoglobin A1c.

In one embodiment, the effective amount is effective to achieve at least a 2 percentage point decrease in hemoglobin A1c.

In one embodiment, the effective amount is effective to achieve at least a 3 percentage point decrease in hemoglobin A1c.

In one embodiment, the effective amount is effective to decrease a fasting blood glucose concentration in said mammal by at least 5 mg/dL.

In one embodiment, the effective amount is effective to decrease a fasting blood glucose concentration in said mammal by at least 10 mg/dL.

In one embodiment, the effective amount is effective to decrease a fasting blood glucose concentration in said mammal by at least 20 mg/dL.

In one embodiment, the naturally occurring material is selected from the group consisting of a hexosamine, glycosaminoglycan, hyaluronic acid, sialic acid, collagen, elastin, other egg proteins or glycoproteins, lysozyme, ovotransferrin, lysyl oxidase, and/or a combination thereof.

In one embodiment, the hexosamine is glucosamine and/or N-acetylglucosamine.

In one embodiment, the glycosaminoglycan is chondroitin sulfate, dermatan sulfate, keratin sulfate, heparin sulfate, and/or a combination thereof.

In one embodiment, the naturally occurring material is water soluble.

In one embodiment, the naturally occurring material is water insoluble.

In one embodiment, the naturally occurring material comprises the following in weight percent:
  a. about 0.25 to about 5 wt % hexosamine;
  b. about 0.3 to about 3 wt % glycosaminoglycan;
  c. about 0.5 to about 5 wt % hyaluronic acid;
  d. about 0.01 to about 2 wt % sialic acid; and/or
  e. about 5 to about 20 wt % collagen.

In one embodiment, the naturally occurring material is an extract.

In one embodiment, the naturally occurring material is a hydrolyzate.

In one embodiment, the naturally occurring material is an isolate.

In one embodiment, the mammal is insulin-dependent.

In one embodiment, the mammal has a fasting blood glucose concentration at least 100 mg/dL and at most 125 mg/dL.

In one embodiment, the mammal is diabetic.

DETAILED DESCRIPTION

Method for Treating a Disease or Condition Associated with Abnormal Glucose Methabolism In one aspect, the invention relates to a method for treating a disease or condition associated with abnormal glucose metabolism in a mammal in need thereof. The method includes orally administering to the mammal an effective amount of a composition. The composition includes a naturally occurring material derived from eggshell membrane or from fowl eggshells.

A disease or condition associated with abnormal glucose metabolism refers to a disease or condition wherein the mammal has abnormal glucose metabolism, as compared to a respective normal mammal having the same gender, weight, height, and/or age as the treated mammal. Typically, abnormal glucose metabolism is characterized by one or a combination of the following factors: abdominal obesity, insulin resistance, glucose intolerance, hypertension, above-normal blood sugar (serum glucose) concentration, and above-normal hemoglobin A1c percentage point.

Examples of a disease or condition associated with abnormal glucose metabolism include insulin resistance, glucose intolerance, glucose non-responsiveness, diabetes mellitus, and/or a combination thereof.

Insulin resistance refers to a failure of the body to respond normally to insulin. Normal fasting insulin levels are considered to be <10 µIU/mL, although there is considerable variability within the population. In subjects suffering from insulin resistance, high blood sugar levels stimulate production of insulin. When a subject is unable to normally process excess insulin, insulin levels rise. Eventually, the subject has high blood sugar levels (hyperglycemia) and high insulin levels (hyperinsulemia). Under these conditions, insulin loses its ability to control fat metabolism, and excessive fats enter the bloodstream (hyperlipidemia). Hyperlipidemia contributes to high blood pressure, heart disease and stroke. Other disorders of insulin resistance, include, but are not limited to, dyslipidemia, (including diabetic dyslipidemia) and full-blown Type 2 diabetes, juvenile diabetes and gestational diabetes.

Common forms of insulin resistance include, for example, skeletal muscle insulin resistance, hepatic insulin resistance and adipose tissue insulin resistance. Metabolic syndrome is a clinical diagnosis considered to be a form of insulin resistance and is generally defined as having any three or more of the following conditions: 1) waist measurement of 40 inches or more for men and 35 inches or more for women, 2) triglyceride levels of 150 milligrams per deciliter (mg/dL) or above, or taking medication for elevated triglyceride levels, 3) HDL cholesterol level below 40 mg/dL for men and below 50 mg/dL for women, or taking medication for low HDL levels, 4) blood pressure levels of 130/85 or above, or taking medication for elevated blood pressure levels, or 5) fasting blood glucose levels of 100 mg/dL or above, or taking medication for elevated blood glucose levels.

The degree of insulin resistance may vary amongst subjects. Insulin resistance typically precedes the development of adult onset diabetes. Insulin resistance is often a precursor to Type 2 diabetes. However, mild or even severe insulin resistance may be found in individuals who will never develop diabetes. Genetic factors contribute to this normal variation in insulin resistance.

Glucose intolerance refers to insufficiency of an insulin secretion response in a mammal due to glucose load and/or reduction of insulin action in skeletal muscles or adipose tissues. Accordingly, the mammal is unable to utilize glucose in blood circulation. In some cases, glucose intolerance is caused by insulin resistance. A glucose intolerant subject may have a serum glucose concentration greater than about 100 mg/dL, greater than about 110 mg/dL, or greater than about 120 mg/dL, as compared to a control serum glucose concentration.

Glucose intolerance is a condition that may precede the onset of diabetes and it may be associated with various metabolic diseases or conditions, such as obesity, hypertension, hypertriglyceridemia, etc. Continuous glucose intolerant conditions may induce onset of diabetes and may also enhance the progress of diabetes. Therefore, treatment of glucose intolerance is considered effective in reducing an incidence or progression of diabetes.

Glucose non-responsiveness refers to the complete inability of cells, islets or mammals to respond to treatment with or administration of glucose, as well as decreased responsiveness to glucose (e.g., by cells that do not produce sufficient levels of insulin in response to glucose or that require significantly higher levels of glucose to respond at normal levels).

Diabetes or diabetes mellitus is a disease that occurs when the body cannot make use of the glucose in the blood for energy because either the pancreas is not able to make enough insulin or the insulin that is available is not effective. There are two main types of diabetes mellitus: insulin-dependent (type 1) and noninsulin-dependent (type 2 or adult onset diabetes). A third type of diabetes is gestational diabetes that develops only in pregnant women.

Method for Reducing Incidence or Progression of Insulin-Dependent Diabetes Mellitus In another aspect, the invention relates to a method for reducing incidence or progression of insulin-dependent diabetes mellitus in a mammal in need thereof. The method includes orally administering to the mammal an effective amount of a composition. The composition includes a naturally occurring material derived from eggshell membrane or from fowl eggshells.

Reducing incidence or progression of the disease or condition refers to alleviation of symptoms, diminishment of extent of disease or condition, stabilized (i.e., not worsening) state of disease or condition, delay or slowing of disease progression, amelioration or palliation of the disease state and remission (whether partial or total), whether detectable or undetectable. For example, mammals with abnormal glucose metabolism typically have a significant risk of developing diabetes. The present invention reduces incidence or progression of the disease or condition, for example, by preventing a transition from abnormal glucose metabolism to insulin-dependent diabetes mellitus in a mammal.

In insulin-dependent diabetes (IDDM; type I diabetes), the pancreas makes little or no insulin because the insulin-producing beta cells have been destroyed. IDDM may occur at any age. Current treatment typically includes daily insulin injections or use of an insulin pump, a planned diet and regular exercise, and daily self-monitoring of blood glucose. If the level of insulin is too low for a long period of time, the body begins to break down its stores of fat for energy. The break down of fat stores causes the body to release fatty acids, which are then converted into ketone bodies or ketoacids that are toxic at high levels. The result is called ketoacidosis, a severe condition that may put a person into a coma if not treated promptly.

Mammal

The present invention is suitable for both medical and veterinary uses. Suitable subjects include, but are not limited to, mammalian and avian subjects; preferably, mammalian subjects; more preferably humans, monkeys, pigs, cattle, dogs, horses, cats, sheep, mice, rats, guinea pigs, rabbits, and goats, and are most preferably human subjects. The mammal may be male or female, of any age.

A mammal in need of the methods of the invention includes those already suffering from the disease or condition, as well as those prone to develop the disease or condition, and those in whom the condition or disorder is to be prevented.

In one embodiment, the mammal is insulin-dependent. An insulin-dependent mammal is one that has been prescribed insulin injections or use of an insulin pump, and/or equivalent treatments.

In another embodiment, the mammal is pre-diabetic. A mammal that is pre-diabetic has a glucose metabolic state that is intermediate between normal glucose homeostasis and metabolism and a metabolic state observed in a respective mammal having diabetes. For example, a mammal that is pre-diabetic typically has a fasting blood glucose concentration at least 100 mg/dL and at most 125 mg/dL typically indicates pre-diabetes. As another example, a mammal that is pre-diabetic typically has a hemoglobin A1c level that is about 6.5% to about 7.0% of total hemoglobin.

In a further embodiment, the mammal is diabetic, suffering from diabetes as described above. A mammal that is diabetic typically has a glucose metabolic state that is abnormal. For example, a mammal that is diabetic typically has a fasting blood glucose concentration at least about 125 mg/dL or greater. As another example, a mammal that is diabetic typically has a hemoglobin A1c level that is at least about 7.0% of total hemoglobin or greater.

Administration

The methods of the invention include orally administering to a mammal in need thereof an effective amount of the composition. For oral administration, the composition may be in the form of any unit dosage vehicle, such as a capsule or tablet, or in the form of powder, liquid, or contained in any convenient food item. The composition may also include pharmaceutically or nutraceutically active ingredients, fillers, binders, lubricants, flow agents, colorants, or other processing agents.

In one embodiment, the effective amount of the composition administered in accordance with the method of the invention is any amount effective for treating a disease or condition associated with abnormal glucose metabolism. In another embodiment, the effective amount of the composition administered in accordance with the method of the invention is any amount effective for reducing incidence or progression of insulin-dependent diabetes mellitus.

The administered amount of the composition will vary according to numerous factors that are well known in the art, such as the disease or condition to be treated or reduced, the route of administration, the particular mammal to be treated, the status of the disease or condition in the subject, etc. The appropriate amount of the composition can readily be determined by those skilled in the art.

For example, the effective amount of the composition may be any amount that is sufficient to achieve a decrease in a percentage point of hemoglobin 1Ac. In one embodiment, the effective amount is effective to achieve at least a 0.2 percentage point, a 1 percentage point, a 2 percentage point, or a 3 percentage point decrease of hemoglobin A1c in the subject. Methods of determining percentage point decrease of hemoglobin A1c in a mammal are known in the art.

In healthy, non-diabetic mammals, the hemoglobin A1c level is typically less than about 6.5%, preferably less than about 6.0%, and more preferably less than about 5.5% of total hemoglobin. Complications of diseases or conditions associated with abnormal glucose metabolism can be reduced, delayed, or treated if the percentage of total hemoglobin A1c is maintained below 6.5%. Accordingly, in one embodiment of the invention, the effective amount is effective to achieve a total hemoglobin A1c level less than about 6.5%, preferably less than about 6.0%, and more preferably less than about 5.5% of total hemoglobin. Consequently, in another embodiment, the effective amount is effective for achieving insulin-independence in an insulin-dependent mammal. See, for example, Example 2.

A mammal in need of a method of the invention may have a hemoglobin A1c level that is greater than about 6.5%, 7.0%, 7.5%, 8.0%, 8.5%, 9.0%, 9.5% of total hemoglobin or greater. A hemoglobin A1c level that is about 6.5% to about 7.0% of total hemoglobin typically indicates pre-diabetes. A hemoglobin A1c level that is greater than about 7.0% typically indicates diabetes. Accordingly, compositions of the present invention may be administered to a mammal with a hemoglobin A1c level equal or greater than about 6.5% of total hemoglobin.

As another example, the effective amount of the composition may be any amount that is sufficient to achieve a decrease in fasting blood glucose concentration in the mammal. A mammal's blood glucose may be measured after fasting for 8 to 12 hours. In one embodiment, the effective amount is effective to decrease a fasting blood glucose concentration in the mammal by at least 5 mg/dL, at least 10 mg/dL, at least 20 mg/dL. Methods of determining a decrease of fasting blood glucose concentration in a mammal are known in the art.

In one embodiment of the invention, the effective amount is effective to achieve a normal fasting blood glucose concentration in the mammal. A mammal with normal fasting blood glucose typically has a fasting blood glucose concentration that is at least 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, or 110 mg/dL. A mammal with normal fasting blood glucose typically has a fasting blood glucose concentration that is less than 120, 119, 118, 117, 116, 115, 114, 113, 112, 111, 110 mg/dL. Any minimum value may be combined with a maximum value in order to describe a range of normal fasting blood glucose concentration for a mammal.

As is known in the art, a mammal having normal fasting blood glucose concentration is typically insulin-independent. Accordingly, in another embodiment, the effective amount is effective for achieving insulin-independence in an insulin-dependent mammal. See, for example, Example 2.

A mammal in need of a method of the invention may have a fasting blood glucose concentration that is greater than about 100, 105, 110, 111, 112, 113, 114, 115, 116, 117, 118, 119, 120, 121, 122, 123, 124, or 125 mg/dL. A fasting blood glucose concentration at least 100 mg/dL and at most 125 mg/dL typically indicates pre-diabetes. A fasting blood glucose concentration greater than 125 mg/dL indicates diabetes. Accordingly, compositions of the present invention may be administered to a mammal with fasting blood glucose concentrations between 110 mg/dL and 125 mg/dL. For example, the mammal in need thereof may have a fasting blood glucose concentration of 110, 111, 112, 113, 114, 115, 116, 117, 118, 119, 120, 121, 122, 123, 124, 125 mg/dL, or greater.

In one embodiment, administration of a composition of the invention decreases fasting blood glucose concentrations to less than 125, 124, 123, 122, 121, 120, 119, 118, 117, 116, 115, 114, 113, 112, 111, and preferably below 110 mg/dL.

The methods of the present invention may be combined with any known treatment or prevention regimen for diseases or conditions associated with abnormal glucose metabolism and diabetes mellitus. The methods and compositions of the invention may be simultaneously, separately or sequentially administered with any known treatment regimens.

In a preferred embodiment, a composition of the present invention may be administered long-term for the methods of the invention. In this regard, the composition may be administered for a period of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days. The compositions may also be administered for an administration period of at least 1, 2, 3, 4, 5, 6, 7, 8, 9, 10, 11, 12 or more months. The compositions may also be administered for an administration period of at least 1, 2, 3, 4, 5, 6, 7 8, 9, 10 or more years. During the administration period, the composition may be administered once daily, twice daily, thrice daily, or periodically, such as every other day, etc.

The composition of the present invention may also be administered intermittently for the methods of the invention. For example, the composition may be administered for an administration period of 1, 2, 3, 4, 5, or more weeks, followed by a period of discontinuance, followed by an administration period of 1, 2, 3, 4, 5 or more weeks.

Composition

The composition used in the methods of the invention includes a naturally occurring material. The terms, "natural material," "naturally occurring material" or "naturally occurring active material" derived from eggshell, eggshell membrane, or a combination thereof refer to material that contains a significant amount of at least one ingredient or component of the eggshell, eggshell membrane, or a combination thereof that is substantially unaltered from an untreated or unprocessed eggshell, eggshell membrane, or a combination thereof, respectively. "Substantially unaltered" refers to a characteristic of a selected or desired ingredient(s) or component(s), having substantially retained its/their physical and/or chemical characteristics and is/are not significantly decomposed, digested or cleaved. However, other components or ingredients may be altered in certain isolates or hydrolysates. For example, hydrolysates prepared by enzyme treatment may result in naturally occurring proteins being at least partially digested.

Preferably, the majority of the naturally occurring ingredients found in the eggshell, eggshell membrane, or a combination thereof are substantially unaltered and, more preferably, substantially all of the naturally occurring ingredients are substantially unaltered. Although the physical characteristics of individual components of the eggshell, eggshell membrane, or a combination thereof remain substantially unaltered, the overall composition or amounts of different components can be altered depending on the desired composition for a particular isolate, extract or hydrolysate.

In one embodiment, the composition may contain a material derived from eggshell, eggshell membrane, or a combination thereof that is processed to be rich in water-soluble fractions of the respective eggshell, eggshell membrane, or a combination thereof that is rich in hyaluronic acid.

In another embodiment, the composition may contain a material derived from eggshell, eggshell membrane, or a combination thereof that is rich in water-insoluble fractions and/or is rich in certain collagens.

The material may also contain a specific component selected from the group consisting of a hexosamine, chondroitin sulfate, hyaluronic acid, collagen, other proteins, and combinations thereof. In one embodiment, the material includes at least about 10 wt % and at most about 80 wt % of other egg proteins or glycoproteins derived from eggshell, eggshell membrane, or a combination thereof, based on total weight of the material. It is also contemplated that the material derived from the eggshell, eggshell membrane, or a combination thereof can be processed to be rich in specific type(s) of collagen and/or proteins, depending upon the intended use.

In an embodiment of the invention, the material contains at least about 0.1 wt %, 0.25 wt %, 0.5 wt %, 1 wt %, 2 wt %, 3 wt %, 4 wt %, or about 4.5 wt % hexosamine, and the material contains at most about 10 wt %, 9 wt %, 8 wt %, 7 wt %, 6 wt %, or about 5 wt % hexosamine, based on the total weight of the material. Any minimum value may be combined with a maximum value in order to describe a range. Preferably, the material includes at least about 0.25 wt % and at most about 5 wt % hexosamine.

Examples of hexosamine include glucosamine, N-acetyl-D-glucosamine, glucosamine hydrochloride, glucosamine sulfate, and combinations thereof. Preferably, the hexosamine is glucosamine or N-acetyl-D-glucosamine.

In another embodiment, the material contains at least about 0.1 wt %, 0.2 wt %, 0.3 wt %, 0.4 wt %, 0.5 wt %, 0.6 wt %, 0.7 wt %, 0.8 wt %, 0.9 wt %, or about 1 wt % glycosaminoglycan, and the material contains at most about 5 wt %, 4 wt %, 3 wt %, 2.5 wt %, 2.0 wt %, or about 1.5 wt % glycosaminoglycan, based on the total weight of the material. Any minimum value may be combined with a maximum value in order to describe a range. Preferably, the material includes at least about 0.3 wt % and at most about 3% glycosaminoglycan.

Examples of a glycosaminoglycan include chondroitin sulfate, dermatan sulfate, keratan sulfate, heparan sulfate, and combinations thereof.

In yet another embodiment, the material contains at least about 0.1 wt %, 0.2 wt %, 0.3 wt %, 0.4 wt %, 0.5 wt %, 1 wt %, 1.5 wt %, 2.0 wt %, 2.5 wt %, 3.0 wt %, 3.5 wt %, 4 wt % or about 4.5 wt % hyaluronic acid, and the material contains at most about 10 wt %, 9 wt %, 8 wt %, 7 wt %, 6 wt %, or about 5 wt % hyaluronic acid, based on the total weight of the material. Any minimum value may be combined with a maximum value in order to describe a range. Preferably, the material includes at least about 0.5 wt % and at most about 5% hyaluronic acid. In a preferred embodiment, the ratio of hyaluronic acid to the other naturally occurring materials in the composition is in the range of about 10:0.1 to about 0.1:10.

In a further embodiment, the material contains at least about 0.01 wt %, 0.02 wt %, 0.03 wt %, 0.04 wt %, 0.05 wt %, 0.06 wt %, 0.07 wt %, 0.08 wt %, 0.09 wt %, or about 0.1 wt % sialic acid, and the material contains at most about 3 wt %, 2.5 wt %, 2.0 wt %, 1.5 wt %, 1.0 wt % or about 0.5 wt % sialic acid, based on the total weight of the material. Any minimum value may be combined with a maximum value in order to describe a range. Preferably, the material includes at least about 0.01 wt % and at most about 2 wt % sialic acid.

In yet a further embodiment, the material contains at least about 1 wt %, 2 wt %, 3 wt %, 4 wt %, or 5 wt % collagen, and the material contains at most about 40 wt %, 35 wt %, 30 wt %, 25 wt %, 20 wt %, 15 wt %, or about 10 wt % collagen, based on the total weight of the material. Any minimum value may be combined with a maximum value in order to describe a range. Preferably, the material includes at least about 5 wt % and at most about 20 wt % collagen. The collagen can be a type selected from the group consisting of Type I collagen, Type V collagen, Type X collagen, and combinations thereof. In a preferred embodiment, the ratio of collagen to the other naturally occurring materials is in the range of about 10:0.1 to about 0.1:10.

The naturally occurring material may be derived from eggshell, eggshell membrane, or a combination thereof.

Eggshell

In one embodiment of the invention, the method includes orally administering to a mammal in need thereof an effective amount of a composition, which includes a naturally occurring material derived from eggshells, preferably fowl eggshells. Eggshell refers to the calcareous portion of eggs from which the eggshell membrane is removed. Suitable eggshells may be obtained from chickens or other birds and fowl, such as, for example, ducks, emu, ostrich, dove, quail, grouse, goose, turkey, ostrich, game hen, squab, pheasant, etc.

In one embodiment, the naturally occurring material derived from eggshell is an eggshell powder. For example, the eggshell material may be pulverized to produce an eggshell powder having a particle size between 100-500 microns. Powdering or pulverizing methods are known in the art.

In another embodiment, the naturally occurring material derived from eggshell is an eggshell extract. In yet another embodiment, the naturally occurring material derived from eggshell is an eggshell hydrolysate. In a further embodiment, the naturally occurring material derived from eggshell is an eggshell isolate.

Eggshell, processed eggshell, and eggshell hydrolysates or isolates contain naturally occurring materials derived from eggshell. These materials can be selected from the group consisting of a hyaluronic acid, hexosamine, chondroitin sulfate, collagen and combinations thereof.

The eggshell, processed eggshell, and eggshell hydrolysates and isolates are preferably free of any animal body components or traces thereof, e.g., animal tissue, blood or body fluid components, which are detrimental or undesirable for the contemplated use of the naturally occurring material or composition.

Eggshell Membrane

In one embodiment of the invention, the method includes orally administering to a mammal in need thereof an effective amount of a composition, which includes a naturally occurring material derived from eggshell membrane. Eggshell membrane is composed of two individual membranes between egg albumin and eggshell. The membranes are primarily comprised of protein fibers. The fibers appear to be a network or scaffold predominantly containing Type I collagen fibers that are encapsulated in a continuous mantle of proteoglycans and other macromolecules. The thickness of the two membranes ranges from 73-114 µm in eggs from White Leghorn and New England pullets. The outer membrane has a thickness ranging from 53.2 µm to 65.5 µm in White Leghorn eggs while the inner membrane ranges form 19.5 µm to 24.3 µm.

The proteins of shell membranes typically exhibit a high content of arginine, glutamic acid, methionine, histidine, cystine, and proline. Eggshell membranes also typically contain hydroxyproline, hydroxylysine, and desmosine. Type I, Type V, and Type X collagen are also typical in eggshell membrane.

Eggshell membrane also has been shown to contain acid glycosaminoglycans including dermatan sulfate and chondroitin-4-sulfate. Sulfated glycoproteins have been isolated from eggshell membrane. Glycoproteins in eggshell membrane include, for example, hexosamines, hexoses, and fucose.

In addition, hyaluronic acid has been detected in eggshell membrane. Other components identified in eggshell membrane include ovotransferrin, desmosine and isodesmosine, lysyl oxidase, and lysozyme.

In one embodiment, the naturally occurring material derived from eggshell membrane is an eggshell membrane powder. For example, the eggshell membrane material may be dehydrated to produce eggshell membrane flakes, which are then pulverized to produce an eggshell membrane powder having a particle size between 100-500 microns. Powdering or pulverizing methods are known in the art, such as, for example, by use of a standard milling or pulverizing procedure to treat eggshell membrane flakes containing about 10% moisture.

In another embodiment, the naturally occurring material derived from eggshell membrane is an eggshell membrane extract. In yet another embodiment, the naturally occurring material derived from eggshell membrane is an eggshell membrane hydrolysate. In a further embodiment, the naturally occurring material derived from eggshell membrane is an eggshell membrane isolate.

Eggshell membrane, processed eggshell membrane, and eggshell membrane hydrolysates or isolates contain naturally occurring materials derived from eggshell membrane. These materials can be selected from the group consisting of a hyaluronic acid, hexosamine, chondroitin sulfate, collagen and combinations thereof.

The eggshell membrane, processed eggshell membrane, and eggshell membrane hydrolysates and isolates are preferably free of any animal body components or traces thereof, e.g., animal tissue, blood or body fluid components, which are detrimental or undesirable for the contemplated use of the naturally occurring material or composition.

Although certain embodiments or examples may be described herein with reference to eggshell membrane, one skilled in the art can ascertain use of fowl eggshells. For example, one skilled in the art can ascertain various methods for processing of eggshells to obtain, extract, and/or purify the naturally occurring materials (i.e., hyaluronic acid, glucosamine, chondroitin sulfate, collagens) from eggshell sources. Such equivalents are intended to be encompassed in the scope of the present invention.

EXAMPLES

The following non-limiting examples have been carried out to illustrate embodiments of the invention.

Example 1

Preparation of Eggshell Membrane Flakes and Powder

The following example relates to the preparation of eggshell membrane flakes and powder. Hen eggshells and attached eggshell membrane were obtained from an egg breaking facility. The eggshell membrane was first separated from eggshells. Eggshell membrane flakes were collected and immediately packaged in plastic bags and placed in storage. Powdering was accomplished using standard milling or pulverizing procedures to treat eggshell membrane flakes containing about 10% moisture. The powder was subsequently sized by screening the pulverized powder through a series of calibrated screens to produce a particle size range from 100-500 microns.

Example 2

Treatment of a Disease Associated with Abnormal Glucose Metabolism in an Insulin-Dependent Diabetic Human Eggshell membrane powder capsules containing about 500 mg of eggshell membrane powder were prepared as described in U.S. patent application Ser. No. 11/943,169. The capsule was administered orally to an insulin-dependent diabetic human once before every meal, daily. After about 90 days, the patient experienced greater blood sugar control with average fasting blood glucose decreasing from 120-130 mg/dL to 110-120 mg/dL. Because the patient was insulin-dependent, hemoglobin A1c was well-controlled in the 6.0-6.5% range. The decrease in fasting blood glucose continued over time and the patient found it necessary to decrease their insulin intake accordingly to avoid fasting hypoglycemia. After about 18 months, the patient was no longer insulin-dependent and was no longer required to take insulin injections nor any oral diabetic medication, other than the eggshell membrane capsule. The patient is now able to control their fasting blood glucose levels through diet and exercise and has normal hemoglobin A1c levels, i.e., less than about 6.5% total hemoglobin.

Example 2

Reduction of Incidence or Progression of Insulin-Dependent Diabetes Mellitus in a Pre-Diabetic Patient Eggshell membrane powder prepared as in Example 1 was placed in capsules containing 500 mg of eggshell membrane powder. The capsule was administered orally to the insulin-dependent diabetic human once before every meal, daily. After about one year, the patient observed a fasting blood glucose that is less than about 120 mg/dL.

Example 3

Method of Identifying Candidate Compound or Candidate Mixture of Compounds in Eggshell, Eggshell Membrane, or a Combination Thereof which Treats and/or Reduces Incidence of or Progression of a Disease or Condition Associated with Abnormal Glucose Metabolism The term "candidate compound" refers to any compound for which evidence of treating and/or reducing incidence of or progression of a disease or condition associated with abnormal glucose metabolism. The term "candidate mixture of compounds" refers to any combination of two and/or more compounds for which evidence of treating and/or reducing incidence of or progression of a disease or condition associated with abnormal glucose metabolism exists.

Examples of compounds include biological molecules and small molecules. Such evidence includes, for example, evidence that the compound or mixture of compounds treats and/or reduces incidence of or progression of a disease or condition associated with abnormal glucose metabolism in a mammal.

A biological molecule is any molecule which contains more than one nucleotide, saccharide, or an amino acid unit, and has a molecular weight greater than about 450. Molecules that contain more than one nucleotide units include nucleic acids, oligonucleotides and polynucleotides. Molecules that contain more than one saccharide unit include disaccharides, trisaccharides, oligosaccharides (more than four saccharides) and polysaccharides. Molecules that contain more than one amino acid units include oligopeptides, peptides, proteins, and polypeptides.

Biological molecules further include derivatives of any of the molecules described above. For example, derivatives of biological molecules include lipid and glycosylation derivatives of molecules that contain more than one amino acid unit, e.g., lipoproteins and glycoproteins. Derivatives of biological molecules further include lipid and glycosylated derivatives of molecules that contain more than one saccharide unit, e.g. lipopolysaccharides and glycopolysaccharides. Derivatives of biological molecules further include proteo-derivatives of molecules that contain more than one nucleotide units.

Small molecules are typically organic compounds, including organometallic and organosilicon compounds, and the like, and generally have molecular weights of approximately 450 or less. Small molecules can further include molecules that would otherwise be considered biological molecules, except their molecular weight is not greater than approximately 450. Thus, small molecules can include monosaccharides, oligosaccharides, amino acids, oligopeptides, nucleotides, oligonucleotides, and their derivatives, having a molecular weight of approximately 450 or less.

A small molecule can have any molecular weight. They are merely called small molecules because they do not qualify as biological molecules, and typically have molecular weights less than approximately 450.

The method for identifying a candidate compound or candidate mixture of compounds includes separating an eggshell membrane from an egg white and eggshell using any suitable mechanical and/or chemical technique known in the art.

The eggshell membrane may be subjected to a solubilization process for solubilizing at least one biological molecule or small molecule from the eggshell membrane. The eggshell membrane may also be subjected to hydrolysis by a suitable means known in the art.

The resulting solubilized or hydrolyzed components can be additional methods to further purify, isolate, and/or concentrate the components. For example, once the proteinaceous material or compounds are solubilized or hydrolyzed, one skilled in the art can use standard biochemistry methods to isolate a protein or compound of interest. Examples of such methods include all types of chromatography (e.g., high pressure liquid chromatography (HPLC) and column chromatography), fractional distillation, and extracting techniques using various solvents. Examples of useful solvents include water, alcohols (e.g., methanol, ethanol, butanol, and propanol), dimethyl sulfoxide, dimethyl formamide, tetrahydrofluan, hexane, ethyl acetate, and chloroform, and/or any mixtures thereof.

The method for identifying a candidate compound or candidate mixture of compounds further includes contacting the compound or mixture of compounds with a gastrointestinal tract cell. The gastrointestinal cell can be any cell type found in the gastrointestinal tract, including, for example, epithelial cells, endothelial cells, smooth muscle cells, endocrine cells, secretory cells, mucosal cells, and absorptive cells of the intestinal epithelium. Gastrointestinal tract cells include, for example, a tonsil cell, esophageal cell, stomach cell, pancreatic cell, pancreatic beta cell, colonic cell, intestinal cell (e.g., small intestinal cell and large intestinal cell), as well as a distal ileum cell. The contacting may be performed via in vitro or in vivo methods.

In vitro methods typically include mixing the compound or mixture of compounds with suitable cells in a culture medium. The order of adding the compound or mixture of compounds and the cells to the culture medium is not critical. The gastrointestinal tract cells may be independent of other cells, or may be associated with other cells.

In vivo methods typically involve the administration of the compound or mixture of compounds, such as those described above, to the gastrointestinal cell of a mammal, preferably a human or laboratory mammal. The compounds or mixture of compounds useful in the methods of the present invention are administered to a mammal in an amount that, for example, decreases hemoglobin A1c levels or decreases fasting blood glucose concentration. The administered amount may vary over a large range, and may be determined during pre-assay tests by methods familiar to one of ordinary skill in the art.

The compound or mixture of compounds useful in the methods of the present invention may be administered to a mammal by any of a number of well-known methods for administering compounds or mixture of compounds. For example, the compound or mixture of compounds may be administered orally (including to laboratory animals by gavage), sublingually, parenterally, enterally, rectally, by suppository, buccally, intravenously, intranasally, intramuscularly, subcutaneously, and/or transdermally. Other routes of administration include intubation, which refers to placement of a nasogastric feeding tube or a gastric feeding tube into the body of a laboratory animal.

After the compound or mixture of compounds has had time, for example, to decrease hemoglobin A1c levels or decrease fasting blood glucose concentration, the method further includes obtaining a biological sample from the mammal, and determining the candidate compound or a candidate mixture of compounds that treats and/or reduces incidence of or progression of a disease or condition associated with abnormal glucose metabolism in a mammal.

What is claimed is:

1. A method of treating diabetes mellitus in a mammal in need thereof consisting essentially of orally administering a therapeutically effective amount of powdered eggshell membrane to said mammal to effectively treat said diabetes mellitus in said mammal.

* * * * *

UNITED STATES PATENT AND TRADEMARK OFFICE
CERTIFICATE OF CORRECTION

| | |
|---|---|
| PATENT NO. | : 8,679,551 B2 |
| APPLICATION NO. | : 13/640607 |
| DATED | : March 25, 2014 |
| INVENTOR(S) | : Kevin J. Ruff |

Page 1 of 1

It is certified that error appears in the above-identified patent and that said Letters Patent is hereby corrected as shown below:

In the Specification

Column 4, Line 46

Now reads: "Abnormal Glucose Methabolism";
Should read: -- Abnormal Glucose Metabolism --.

Signed and Sealed this
Twelfth Day of August, 2014

Michelle K. Lee
*Deputy Director of the United States Patent and Trademark Office*